(12) United States Patent
Sack et al.

(10) Patent No.: US 10,466,331 B2
(45) Date of Patent: Nov. 5, 2019

(54) ELASTOGRAPHY DEVICE AND ELASTOGRAPHY METHOD

(71) Applicants: Ingolf Sack, Berlin (DE); Juergen Braun, Berlin (DE); Sebastian Hirsch, Berlin (DE); Tassilo Heinze, Wurzen (DE)

(72) Inventors: Ingolf Sack, Berlin (DE); Juergen Braun, Berlin (DE); Sebastian Hirsch, Berlin (DE); Tassilo Heinze, Wurzen (DE)

(73) Assignee: THEA-Devices GmbH, Wurzen (DE)

( * ) Notice: Subject to any disclaimer, the term of this patent is extended or adjusted under 35 U.S.C. 154(b) by 935 days.

(21) Appl. No.: 15/043,916

(22) Filed: Feb. 15, 2016

(65) Prior Publication Data

US 2016/0274210 A1    Sep. 22, 2016

(30) Foreign Application Priority Data

Mar. 18, 2015   (DE) .......................... 10 2015 204 868

(51) Int. Cl.
| | | |
|---|---|---|
| *G01R 33/563* | (2006.01) | |
| *A61B 5/00* | (2006.01) | |
| *A61B 5/055* | (2006.01) | |

(52) U.S. Cl.
CPC ...... *G01R 33/56358* (2013.01); *A61B 5/0051* (2013.01); *A61B 5/055* (2013.01)

(58) Field of Classification Search
CPC ............ G01R 33/56358; A61B 5/0051; A61B 5/0055
See application file for complete search history.

(56) References Cited

U.S. PATENT DOCUMENTS

| 4,472,628 A | * | 9/1984 | Whitten ................. G02B 26/02 |
|---|---|---|---|
| | | | 250/227.14 |
| 5,540,052 A | * | 7/1996 | Sieke ...................... F15B 21/12 |
| | | | 108/27 |

(Continued)

FOREIGN PATENT DOCUMENTS

| DE | 10 2011 017 778 A1 | 10/2012 |
|---|---|---|
| DE | 10 2011 089 401 A1 | 6/2013 |

(Continued)

OTHER PUBLICATIONS

T. Numano et al., "Magnetic Resonance Elastography with an air ball-vibrator"; Proc. Intl. Soc. Mag. Reson. Med 19 (2011); p. 1484.

*Primary Examiner* — Jason Skaarup
(74) *Attorney, Agent, or Firm* — Gordon Rees Scully; Mansukhani, LLP

(57) ABSTRACT

The invention relates inter alia to an elastography device having at least one excitation unit (10) for generating mechanical tissue movements in human or animal tissue, and an image-recording device.

Figure 1:
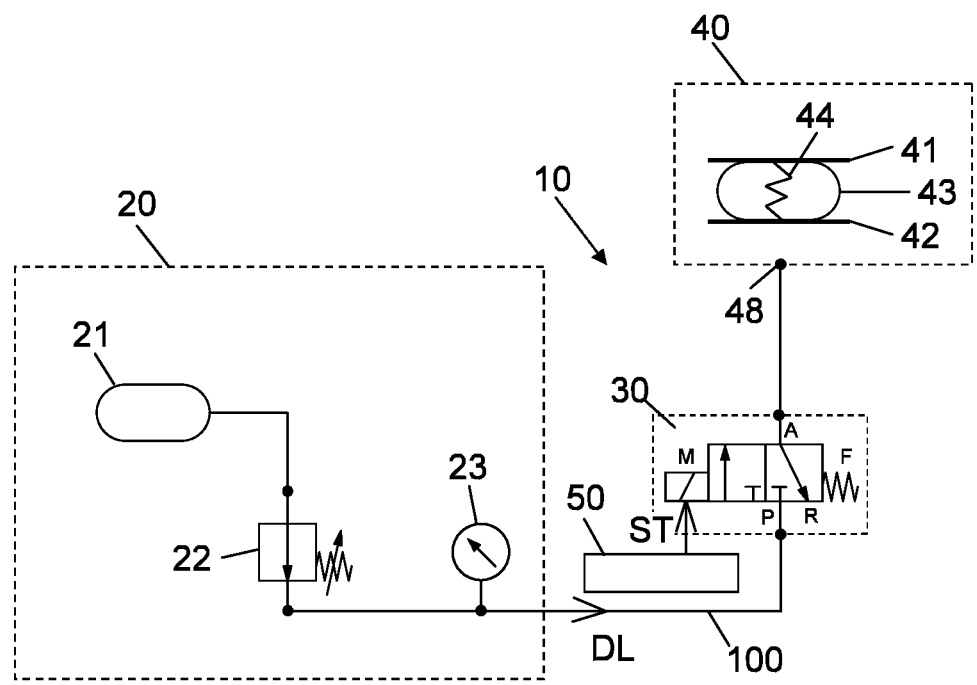

It is provided according to the invention that the excitation unit (10) has: at least one pressure source (20, 20a), at least one pressure-dependently operating actuator (40, 60, 70, 200) for generating mechanical movements, at least one controllable valve (30, 300, 310, 400) which is arranged between pressure source (20, 20a) and actuator (40, 60, 70, 200) in terms of gas flow and the valve position of which influences the pressure acting on the actuator (40, 60, 70, 200), and a control device (50) which is connected to a control port of the valve (30, 300, 310, 400) and which actuates the valve (30, 300, 310, 400) and defines the valve position thereof and, in order to generate the mechanical (Continued)

tissue movements, varies the valve position, and thus the pressure acting on the actuator (40, 60, 70, 200), over the course of time.

13 Claims, 9 Drawing Sheets

(56) References Cited

U.S. PATENT DOCUMENTS

| | | | |
|---|---|---|---|
| 8,281,663 B2 | 10/2012 | Ehman et al. | |
| 2005/0270029 A1* | 12/2005 | Ehman | G01R 33/56358 |
| | | | 324/318 |
| 2009/0209847 A1* | 8/2009 | Li | A61B 5/055 |
| | | | 600/421 |
| 2009/0299168 A1 | 12/2009 | Ehman et al. | |
| 2010/0045289 A1* | 2/2010 | Chopra | G01R 33/28 |
| | | | 324/307 |
| 2010/0130856 A1 | 5/2010 | Sack et al. | |
| 2010/0241012 A1* | 9/2010 | Yin | A61B 5/055 |
| | | | 600/485 |
| 2011/0006767 A1 | 1/2011 | Sack et al. | |
| 2011/0025333 A1* | 2/2011 | Ehman | G01R 33/56358 |
| | | | 324/318 |
| 2012/0053450 A1* | 3/2012 | Salcudean | A61B 5/0051 |
| | | | 600/421 |
| 2013/0303882 A1* | 11/2013 | Kolipaka | A61B 5/0555 |
| | | | 600/415 |
| 2014/0159725 A1 | 6/2014 | Sack et al. | |
| 2014/0350399 A1 | 11/2014 | Sack et al. | |
| 2015/0297311 A1* | 10/2015 | Tesar | G02B 21/16 |
| | | | 600/411 |
| 2017/0332937 A1* | 11/2017 | Kolipaka | A61B 5/055 |

FOREIGN PATENT DOCUMENTS

| | | |
|---|---|---|
| WO | WO 2007/118710 A1 | 10/2007 |
| WO | WO 2008/135588 A2 | 11/2008 |

* cited by examiner

ELASTOGRAPHY DEVICE AND ELASTOGRAPHY METHOD

The invention relates to an elastography device and to an elastography method.

In elastography devices, for example in ultrasound and magnetic resonance elastography, excitation units are used to generate mechanical tissue movements in human or animal tissue.

In the case of magnetic resonance imaging (MRI), sectional images of the inside of the body are created with the aid of strong magnetic fields. MRI operates using radio frequency waves which are radiated in in the simultaneous presence of strong magnetic field gradients. With the exception of organs with low water content, such as bones, MRI provides precise images of all other organs and tissues, and thus makes it possible to identify and assess the position and extent of pathological tissue changes.

Soft tissues such as the brain, internal organs, blood vessels, muscles, tendons, ligaments and cartilage structures can be displayed particularly effectively using MRI. Aside from the purely anatomical imaging, MRI offers a broad spectrum of methods for identification of functional metabolic processes in the brain, the analysis of directional fiber orientations, the assessment of the beating heart, and the quantitative determination of mechanical tissue parameters with the aid of magnetic resonance elastography (MRE).

For MRE, it is necessary, analogously to manual palpation, for forces to be transmitted to the tissue to be examined. For this purpose, by way of mechanical excitation, periodic tissue deflections are induced, the detection of which is performed synchronously to the excitation by way of a specially developed phase contrast technique. The instantaneous local vibration amplitude is in this case encoded in the phase of the complex MR signal. The maps, recorded in time-resolved fashion, of the tissue distortion can be mathematically processed and then provide information regarding viscoelastic properties. Through the measurement of the distortion in all spatial directions, it is possible for mechanical characteristic variables, such as the complex shear modulus, the Young's modulus or the compressive modulus, including their direction dependency, to be fully quantified.

New developments in MRE technology at Charité have contributed to a situation in which, for the first time, it is possible to record highly spatially resolved elasticity maps of organs, which could revolutionize in particular the non-invasive mechanical characterization of neurodegenerative and fibrous diseases, and of tumors. An important criterion for the quality of the elasticity maps calculated by way of physical modeling and inversion methods is the ratio of phase noise to the size of the distortion amplitude encoded in the phase images. The latter can be controlled directly by way of the motion encoding gradients, which are limited in amplitude, and by way of the amplitude of the mechanical excitation.

At present, in MRE, different types of mechanical excitation units (actuators) are used to generate deflections in tissues. These are:

Actuators which are based on the length expansion of piezoelectric crystals.

Actuators which are based on a movement deflection of current-carrying coils moving in the magnetic field of the tomograph.

Actuators in which modified loudspeakers are used and the transmission of force is performed by way of linkages. For example, an acoustomechanical movement transducer for magnetic resonance elastography is known from the German laid-open specification DE 10 2006 037 160.

The use of low-frequency vibrations in the range from 25-80 Hz is physiologically harmless. Example calculations for previous actuators have shown that the values attained in MRE for the sound pressure are lower, approximately by a factor of 100, than in the case of ultrasound examinations that are permissible during the course of a pregnancy.

Hardware modifications by MRI manufacturers and method developments in MRE and the increasing use thereof for patient examinations have led to new challenges in the development of actuators:

1) Intensity of the Mechanical Excitation:

In general, nowadays, many MRI patients are obese. As a result, for many elastography examinations, intense vibration amplitudes are required in order to compensate for the damping of the shear waves over relatively long propagation paths in the tissue. Furthermore, the manufacturers have allowed for the weight development of the population and have developed tomographs with increased opening diameters. As a result, in recent years, the encoding efficiency for tissue vibrations decreased by up to 50%, which can be compensated only by way of powerful MRE actuators. All of the conventional excitation systems mentioned above are limited in terms of their power and cannot realize the excitation intensities that would be required for many MRE examinations in obese patients.

2) Manufacturer-Independent Excitation System:

Signal-optimized MRI hardware with close geometric adaptation to the body geometry offers progressively less space for the integration of actuators. Previous solutions provided close contact of the actuator with the body part under examination (head, abdomen) and had to be adapted to the coil dimensions predefined by the manufacturer. Every new generation of appliances and change between manufacturers necessitated an adaptation of the actuator geometry to the changed hardware requirements. For reasons of economy and method similarity, a manufacturer-independent or at least more manufacturer-independent excitation system than previously will be desirable in future.

3) Universal Excitation System:

Previous actuators have to be adapted on an organ-specific basis, in order to permit, for example, MRE examinations of the brain, of the liver or of the prostate.

4) Simple Construction:

In the case of conventional methods, the force for vibration excitation is generated in the actuator system, which necessitates high levels of electrical power and complex mechanical fittings.

The invention is based on the object of specifying an elastography device with optimized excitation unit.

Said object is achieved according to the invention by way of an elastography device having the features as per patent claim 1. The subclaims specify advantageous refinements of the elastography device according to the invention.

Accordingly, it is provided according to the invention that the excitation unit has: at least one pressure source, at least one pressure-dependently operating actuator for generating mechanical movements, at least one controllable valve which is arranged between pressure source and actuator in terms of gas flow and the valve position of which influences the pressure acting on the actuator, and a control device which is connected to a control port of the valve and which actuates the valve and defines the valve position thereof and, in order to generate the mechanical tissue movements, varies the valve position, and thus the pressure acting on the actuator, over the course of time.

A major advantage of the elastography device according to the invention can be seen in the fact that the force for vibration excitation is generated outside the actuator, and the pressure source and the actuator are separate components which can be optimized individually. For example, it is advantageously possible for particularly powerful force sources (for example in the form of compressed air) to be used for the compensation of weak motion encoding gradients or if particularly large penetration depths are required. Owing to the excitation strength that can be achieved with the invention, adequate wave amplitudes in the body tissue under examination is ensured even in the case of remote positioning (for example on the thorax for brain MRE examinations), and a universally usable MRE excitation system for all organs is made available for the first time.

A further major advantage of the elastography device according to the invention consists in that the actuation of the valve can be performed in the low-voltage range (up to approximately 24 Volts).

It is also advantageous that transient, in particular periodic transient, shockwaves can be generated without cumbersome electronics and merely by way of corresponding valve actuation.

In principle, use may be made of continuously adjustable valves, but valves which operate in multi-stage fashion, in particular in two-stage fashion, are considered to be particularly advantageous because the latter, while having low production costs, can be of mechanically highly stable design and are durable.

The valve can preferably be moved into a rest position in which it separates the actuator from the pressure source and charges the actuator with ambient pressure, in particular connects the actuator to the ambient air in terms of gas flow. In the case of such an embodiment, an actuator return movement can be effected by way of a switchover to ambient pressure.

The control device is preferably designed so as to move the valve alternately over the course of time into a pressurization position, in which the valve transmits the pressure of the pressure source onward to the actuator, or into a rest position, in which the valve separates the actuator from the pressure source and charges the actuator with ambient pressure.

With regard to elastography and with regard to optimum image recording results, it is considered to be advantageous if the control device is designed such that, by actuation of the valve, said control device generates at the pressure inlet of the actuator a pressure profile which is of rectangular or pulsed form over the course of time.

The valve is preferably an electrically controllable solenoid valve or is a valve device having at least one electrically controllable solenoid valve.

The pressure source is preferably a constant-pressure source.

The pressure source is preferably a positive-pressure source, in particular a compressed-air source; it may alternatively, but likewise advantageously, be provided that the pressure source is a negative-pressure source, in particular a vacuum device.

A first pressure line preferably connects the pressure source to the valve and charges the valve with a constant pressure. A second pressure line preferably connects the valve to the actuator and charges the actuator, in a manner dependent on the valve position of the valve, with a pressure which is variable over the course of time.

A further preferred embodiment provides that the actuator has two pressure inlets which are each connected by way of a valve to the pressure source, and the control device is designed such that, to generate the mechanical tissue movements, it moves the two valves in each case alternately over the course of time into a pressurization position, in which the valve transmits the pressure of the pressure source onward to the actuator, or into a rest position, in which the valve separates the actuator from the pressure source and charges the actuator with ambient pressure, the two valves being actuated in each case oppositely over the course of time such that in each case one of the two valves is situated in the pressurization position and the respective other is situated in the rest position.

Another, likewise preferred embodiment provides that the actuator has a first pressure inlet and a second pressure inlet, the valve, in a first valve position, connects the first pressure inlet to a positive-pressure source and connects the second pressure inlet to a negative-pressure source and, in a second valve position, connects the first pressure inlet to the negative-pressure source and connects the second pressure inlet to the positive-pressure source, and the control device is designed such that, to generate the mechanical tissue movements, it switches the valve alternately from the first valve position into the second valve position and from the second valve position into the first valve position.

The actuator is preferably a bellows-cylinder-type actuator, a cushion-type actuator, a drum-type actuator or a shuttle body actuator, in particular a shuttle piston actuator.

The valve is preferably a directional valve, in particular a 3/2 directional valve or a 4/2 directional valve, or a valve device which comprises at least inter alia a directional valve, in particular a 3/2 directional valve or a 4/2 directional valve.

The invention also relates to an elastography method in which mechanical tissue movements are generated in human or animal tissue by way of at least one excitation unit, and images of the tissue are recorded by way of an image-recording device.

According to the invention, with regard to an elastography method of said type, it is provided that, by way of a pressure source, pressure is generated and transmitted onward to at least one controllable valve which is connected, at the outlet side, to a pressure-dependently operating actuator, and the valve position of the valve is varied over the course of time, whereby the actuator generates a mechanical movement which is coupled into the tissue.

Figure 2:
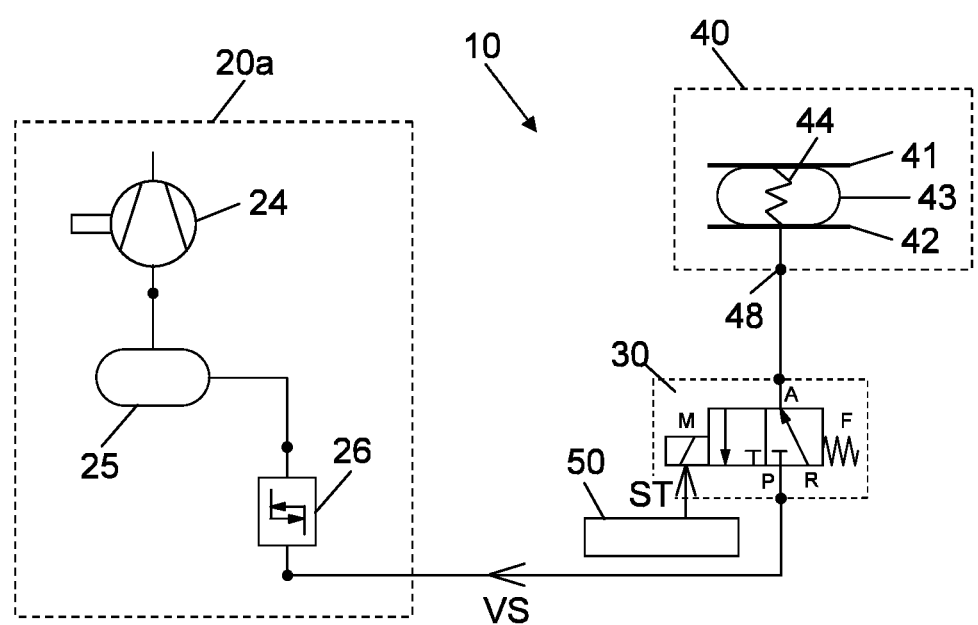
Figure 3:
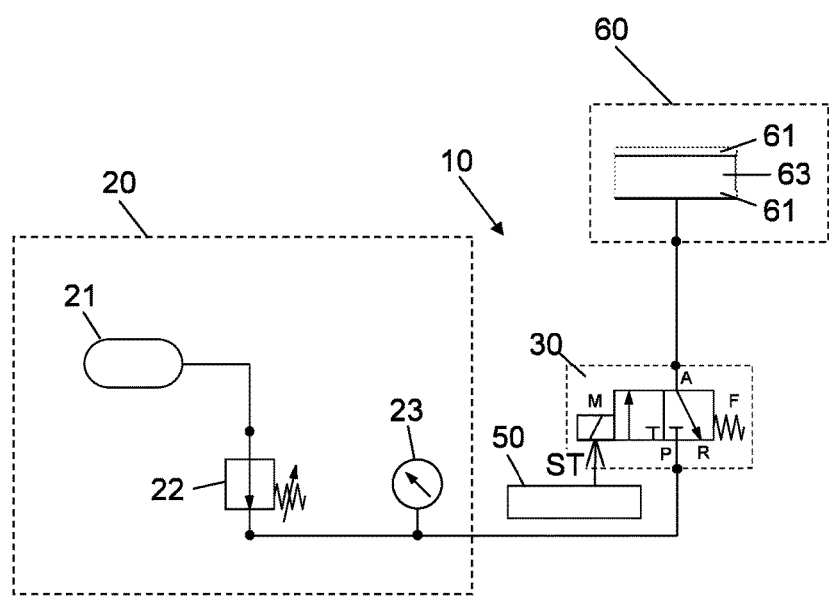
Figure 4:
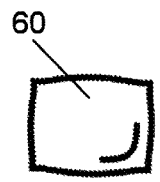
Figure 5:
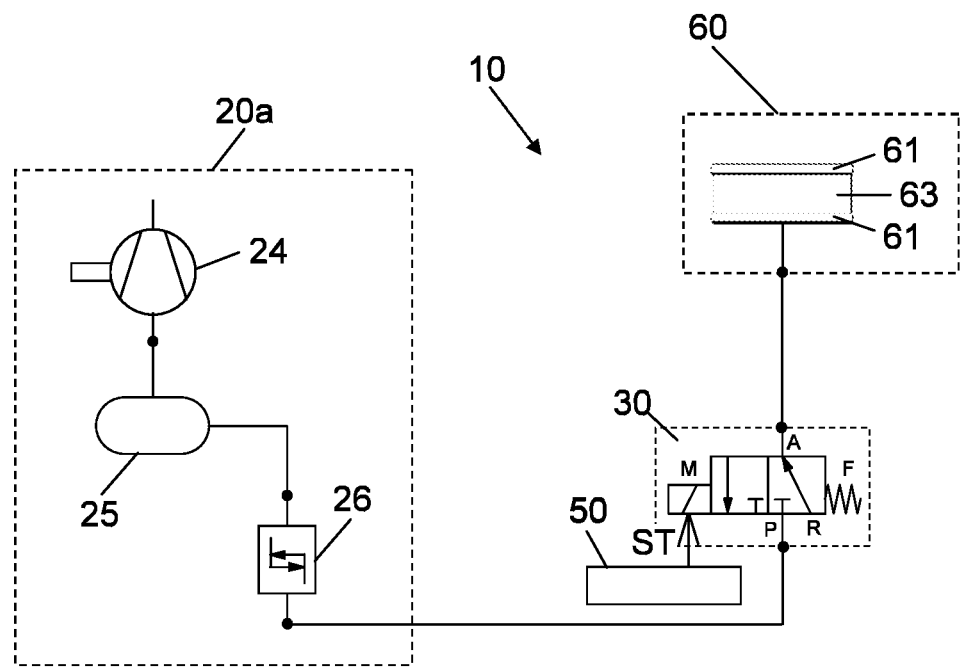
Figure 6:
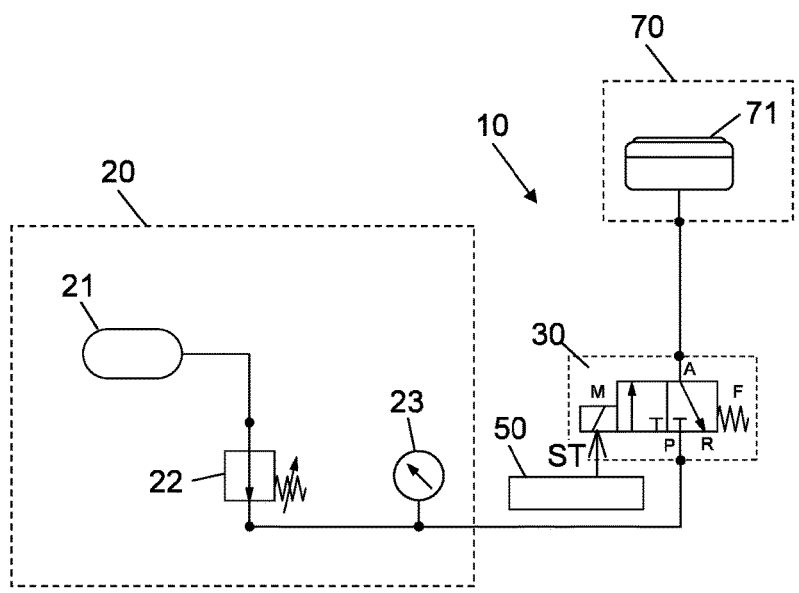
Figure 7:
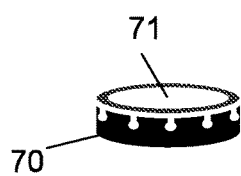
Figure 8:
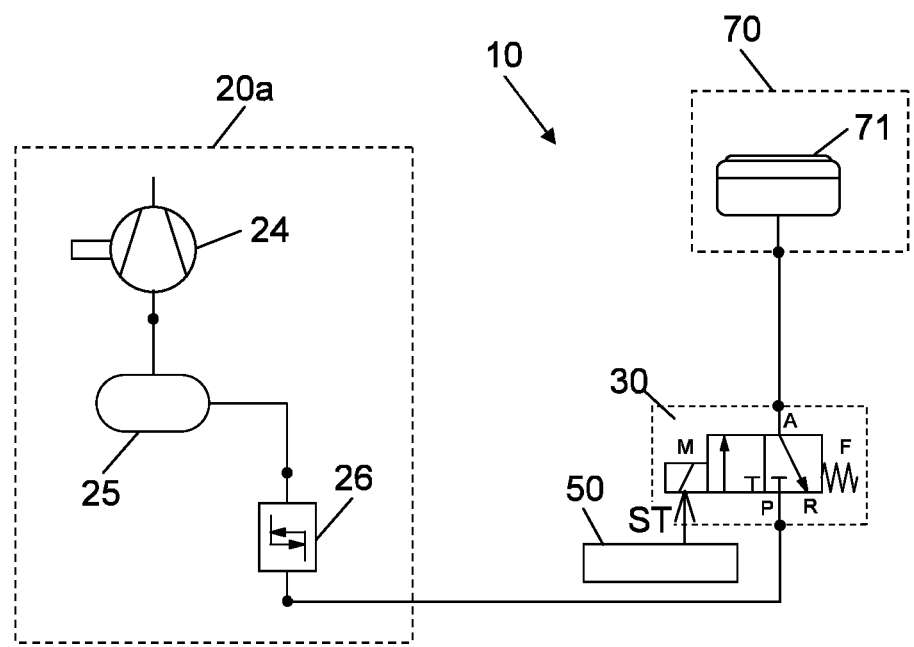
Figure 9:
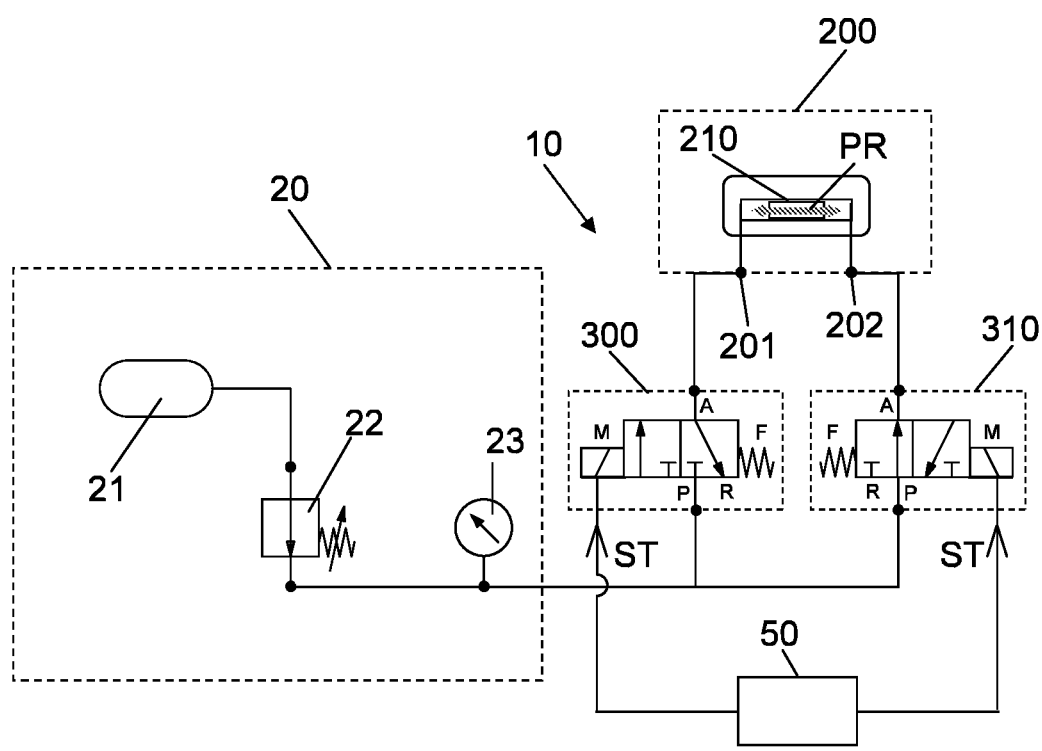
Figure 10:
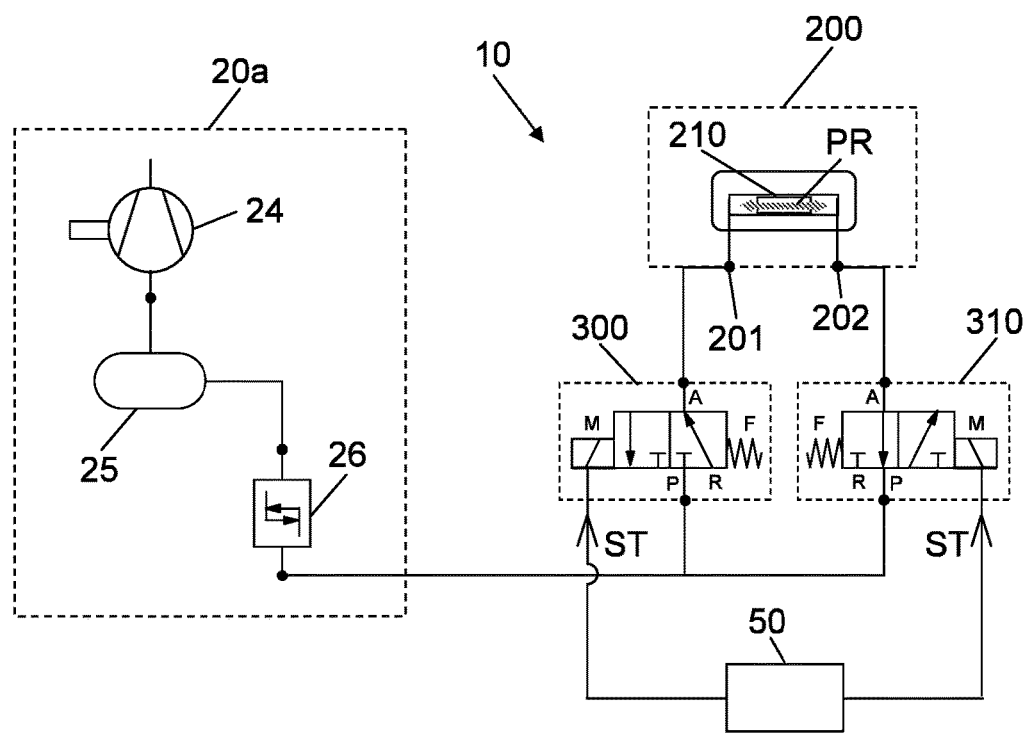
Figure 11:
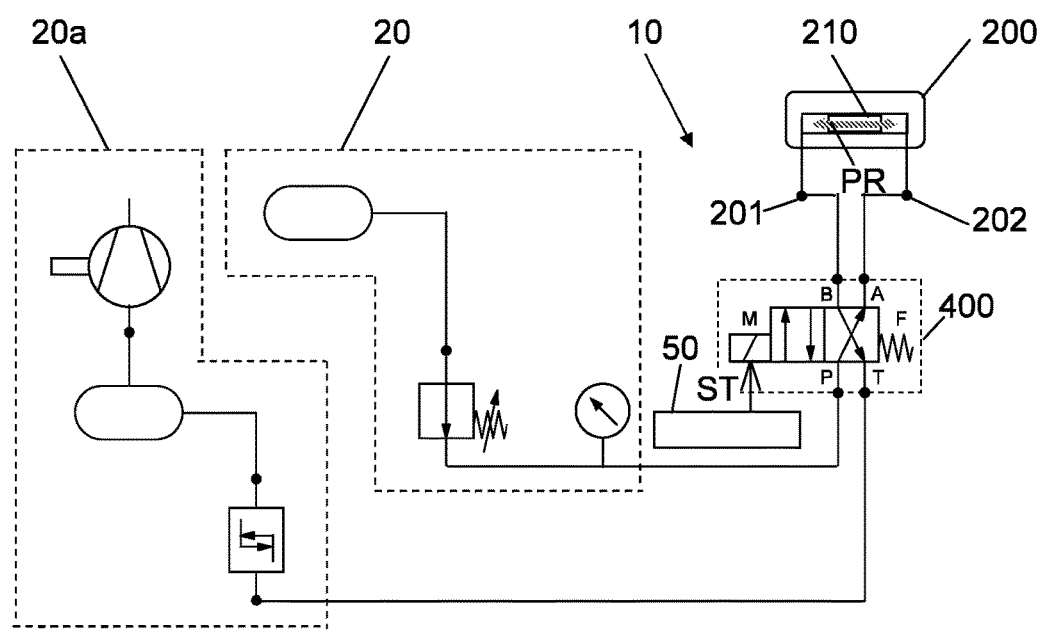

The invention will be discussed in more detail below on the basis of exemplary embodiments; here, in the figures, by way of example:

FIG. 1 shows an exemplary embodiment of an excitation unit for an elastography device, which has a positive-pressure source and a bellows-cylinder-type actuator, FIG. 2 shows an exemplary embodiment of an excitation unit having a negative-pressure source and having a bellows-cylinder-type actuator, FIG. 3 shows an exemplary embodiment of an excitation unit having a positive-pressure source and having a cushion-type actuator, FIG. 4 shows the cushion-type actuator for the excitation unit as per FIG. 3 in a plan view, FIG. 5 shows an exemplary embodiment of an excitation unit having a negative-pressure source and having a cushion-type actuator, FIG. 6 shows an exemplary embodiment of an excitation unit having a positive-pressure source and having a drum-type actuator, FIG. 7 shows the drum-type actuator as per FIG. 6 in a three-dimensional illustration obliquely from the side, FIG. 8 shows an exemplary embodiment of an excitation unit having a negative-pressure source and having a drum-type actuator, FIG. 9 shows an exemplary embodiment of an excitation unit having a positive-pressure source, having a shuttle body actuator and having two valves, FIG. 10 shows an exemplary embodiment of an excitation unit having a negative-pressure source, having a shuttle body actuator and having two valves, and FIG. 11 shows an exemplary embodiment of an excitation unit having a positive-pressure source, having a negative-pressure source, having a valve and having a shuttle body actuator.

In the figures, for clarity reasons, identical or similar components are always denoted by the same reference designations.

FIG. 1 shows an excitation unit 10 for an elastography device which, in addition to the excitation unit 10 as per FIG. 1, has an image-recording device which, for clarity reasons, is not illustrated in any more detail in FIG. 1.

The excitation unit 10 has a pressure source in the form of a positive-pressure source 20 which comprises a compressed-air reservoir 21, a reducing valve 22 and a manometer 23. The compressed-air reservoir 21 may for example be a compressed-air bottle or a compressed-air line, which is fed by a compressor (not shown).

A solenoid valve 30, which is a 3/2 directional valve, is connected to the positive-pressure source 20. The solenoid valve 30 has an electrical solenoid drive M which is equipped with at least one magnet and at least one coil and which can be actuated by way of an externally applied control signal ST.

The solenoid valve 30 furthermore has a restoring spring F which effects a return movement of the solenoid valve 30 into a predefined position when no control signal ST is applied to the solenoid drive M.

An outlet port A of the solenoid valve 30 is connected to a bellows-cylinder-type actuator 40 which has two outer parallel plates 41 and 42 and, situated between these, an elastically deformable bellows 43. The spacing between the two plates 41 and 42 is determined by the pressure within the elastically deformable bellows 43.

For the actuation of the solenoid valve 30, a control device 50 is connected to the electrical solenoid drive M of the solenoid valve 30, which control device generates the abovementioned control signal ST. The control signal ST defines the valve position assumed by the solenoid valve 30.

In the exemplary embodiment as per FIG. 1, the solenoid valve 30 can assume a pressurization position, in which the solenoid valve 30 transmits the pressure of the positive-pressure source 20 onward to the bellows-cylinder-type actuator 40. In the pressurization position, the outlet port A of the solenoid valve 30 is connected to an inlet port P of the solenoid valve 30.

Alternatively, by way of the control signal ST, the solenoid valve 30 can be moved into a rest position in which it separates the bellows-cylinder-type actuator 40 from the positive-pressure source 20 and charges the bellows-cylinder-type actuator with ambient pressure. In the rest position of the solenoid valve 30, the outlet port A is connected to a ventilation port R of the solenoid valve 30.

For the generation of mechanical tissue movements, the bellows-cylinder-type actuator 40 is connected indirectly or directly to human or animal tissue; for example, the bellows-cylinder-type actuator 40 may be placed directly onto a tissue section. For clarity reasons, the tissue is not illustrated in any more detail in FIG. 1.

The excitation unit 10 as per FIG. 1 can be operated, for example, as follows:

By way of the positive-pressure source 20, compressed air DL is generated, which passes to the inlet port P via a compressed-air line 100. If the solenoid valve 30 is situated in the pressurization position, the compressed air DL is transmitted onward to the bellows-cylinder-type actuator 40, whereby the elastically deformable bellows 43 is inflated. The spacing between the two plates 41 and 42 is accordingly increased.

By contrast, if the solenoid valve 30 is situated in the rest position, the compressed air stored in the elastic bellows 43 is discharged to the outside via the ventilation port R, such that the pressure in the bellows 43 falls and the plates 41 and 42 move toward one another.

By virtue of the solenoid valve 30 being switched over from the pressurization position into the rest position and vice versa, it is thus possible to realize a mechanical movement of the two plates 41 and 42 relative to one another, and thus a mechanical tissue movement in the tissue that is connected to the bellows-cylinder-type actuator 40.

With regard to an elastography method being carried out in optimum fashion, it is considered to be particularly advantageous for the control device 50 to generate the control signal ST in rectangular or pulsed fashion, and to thus generate a rectangular or pulsed pressure profile at the outlet port A of the solenoid valve 30 and at the pressure inlet 48 of the bellows-cylinder-type actuator 40. In other words, it is considered to be advantageous for the pressure profile with respect to time within the bellows-cylinder-type actuator 40 to be of rectangular or pulsed form, or to be of at least approximately rectangular or at least approximately pulsed form.

As a solenoid valve 30, use is preferably made of a solenoid valve which exhibits fast switching (for example up to 100 Hz) and the voltage supply of which (preferably 24 V) is switched for example by way of a rectangular signal, generated by way of a function generator, with the desired vibration frequency (5-100 Hz, in the exemplary embodiment 20-50 Hz in 5 Hz increments and, for example, 50% duty cycle). The valve (size: for example 20×80×160 mm$^3$) generates no disturbance signals and can be installed fixedly in the examination room in the vicinity of the tomograph and of a pressure line. As downstream, passive vibration transmission systems connected by way of a preferably flexible pressure hose (Ø=for example 6-8 mm), use may be made of a variety of apparatuses, for example the preferably non-magnetic bellows-cylinder-type actuator 40 that is shown, or other preferably non-magnetic systems, further exemplary embodiments of which will be discussed further below.

FIG. 2 shows an exemplary embodiment of an excitation unit 10 which has a negative-pressure source 20a as pressure source. The negative-pressure source 20a comprises a vacuum pump 24, a negative-pressure tank 25 and a two-position switch for regulation 26 (reducing valve 22 and a manometer 23).

The bellows-cylinder-type actuator 40 of the excitation unit 10 as per FIG. 2 has, in addition to the two plates 41 and 42 and the elastically deformable bellows 43, at least one non-metallic spring element 44 which is arranged in the interior of the bellows 43 and which effects a return movement of the bellows-cylinder-type actuator 40, or a return movement of the two plates 41 and 42 relative to one another, when the bellows-cylinder-type actuator 40 is unpressurized or if the pressure inlet 48 of the bellows-cylinder-type actuator 40 is connected to the ventilation port R of the solenoid valve 30.

The mode of operation of the excitation unit 10 as per FIG. 2 corresponds substantially to the mode of operation of the excitation unit 10 as per FIG. 1, with the difference that, for the generation of mechanical tissue movements, use is made of negative pressure instead of positive pressure. To generate the mechanical tissue movements, the control device 50 will generate a control signal ST with a rectangular or pulsed profile with respect to time, and thus move the solenoid valve 30 from the pressurization position into the rest position or vice versa with a rectangular or pulsed profile with respect to time.

When the solenoid valve 30 is situated in the pressurization position, the air situated in the bellows 43 is drawn out through the solenoid valve 30, such that the spacing between the two plates 41 and 42 is reduced, owing to the negative pressure of the negative-pressure source 20a. If the solenoid valve 30 is moved into the rest position, the spring element 44 within the bellows 43 effects a return movement of the bellows 43 or a return movement of the plates 41 and 42 relative to one another, whereby air is drawn in from the surroundings through the ventilation port R and conducted into the bellows 43.

FIG. 3 shows an exemplary embodiment of an excitation unit 10 which is equipped with a positive-pressure source 20 and a cushion-type actuator 60. The cushion-type actuator 60 comprises an outer cushion wall 61 which encases the cushion interior 63. By variation of the volume within the cushion-type actuator 60, it is possible for a mechanical movement to be generated which can be coupled into human or animal tissue and which thus makes it possible to carry out an elastography method by way of an image-recording device (not illustrated). The charging of the cushion-type actuator 60 with compressed air and the evacuation of the cushion-type actuator 60 are performed by actuation of the solenoid valve 30 by way of a control signal ST that is generated by the control device 50. The excitation unit 10 as per FIG. 3 can be operated in the manner that has already been discussed in detail above in conjunction with FIG. 1. The statements made in conjunction with FIG. 1 thus apply correspondingly to the excitation unit 10 as per FIG. 3.

FIG. 4 shows the cushion-type actuator 60 in the excitation unit 10 as per FIG. 3 in a plan view. The upper cushion wall 61 of the cushion-type actuator 60 can be seen.

FIG. 5 shows an excitation unit 10 having a cushion-type actuator 60 which is operated by way of a negative-pressure source 20a. The negative-pressure source 20a may correspond to the negative-pressure source 20a of the excitation unit 10 as per FIG. 2, such that reference may be made to the above statements relating to FIG. 2.

To permit a return movement of the cushion-type actuator 60 into a predefined initial position when the pressure inlet of the cushion-type actuator 60 or the outlet port A of the solenoid valve 30 is connected to the ventilation port R, the cushion-type actuator 60 is equipped with at least one non-metallic spring element 64 which effects a return movement of the cushion-type actuator 60 into a predefined initial position in the presence of ambient pressure.

For the operation of the excitation unit 10 as per FIG. 5, the control device 50 generates a control signal ST by means of which the solenoid valve 30, which may correspond to the solenoid valve 30 as per FIGS. 1 to 3, is switched from the pressurization position into the rest position and vice versa, whereby the cushion-type actuator 60 is filled with ambient air or is evacuated by suction. By way of the aeration and evacuation by suction, a mechanical movement is generated by way of the cushion-type actuator 60, which mechanical movement can be coupled into human or animal tissue. In this regard, the above explanations relating to FIG. 2 apply correspondingly.

FIG. 6 shows an excitation unit 10 which corresponds substantially to the excitation unit 10 as per FIGS. 1 and 3, because said excitation unit likewise has a positive-pressure source 20 and likewise has a solenoid valve 30 in the form of a 3/2 directional valve. The excitation unit 10 as per FIG. 6 differs merely in that, instead of the bellows cylinder 40 as per FIG. 1 and instead of the cushion-type actuator 60 as per FIG. 3, a drum-type actuator 70 is used. The drum-type actuator 70 has an elastic diaphragm 71. By virtue of the solenoid valve 30 being moved, by way of the control signal ST, into the pressurization position and into the rest position, the diaphragm 71 can be set in motion or in oscillation, which motion or oscillation can be coupled into human or animal tissue in order to make it possible to perform an elastography method by way of an image-recording device (not shown).

FIG. 7 shows the drum-type actuator 70 as per figure in a three-dimensional illustration obliquely from the side.

FIG. 8 shows an exemplary embodiment of an excitation unit 10 having a drum-type actuator 70 and having pressurization by way of a negative-pressure source 20a. With regard to the mode of operation of the excitation unit 10 as per FIG. 8, reference is made to the statements relating to FIGS. 2 and 5, in which it is likewise the case that a negative-pressure source 20a is used for the actuation of the actuator 40 or 60 respectively. The explanations relating to FIGS. 2 and 5 thus apply correspondingly to design variant 8.

FIG. 9 shows an excitation unit 10 having a positive-pressure source 20 which is connected to a shuttle body actuator 200 by way of a first solenoid valve 300 and by way of a second solenoid valve 310 which is connected in parallel with respect to the first solenoid valve. The two solenoid valves 300 and 310 may be identical to the solenoid valves 30 as per FIGS. 1 to 8. In other words, the two solenoid valves 300 and 310 may be solenoid-type 3/2 directional valves which can be moved either into a pressurization position or into a rest position, as has already been discussed above in conjunction with FIGS. 1 to 8.

The shuttle body actuator 200 has two pressure inlets, specifically a first pressure inlet 201 and a second pressure inlet 202. The first pressure inlet 201 is connected to the outlet port A of the first solenoid valve 300. The second pressure inlet 202 is connected to the outlet port A of the second solenoid valve 310.

The shuttle body actuator 200 is equipped with a shuttle body 210, which may for example be a movable piston. The shuttle body 210 is displaceable from left to right, and in the reverse direction from right to left, along the arrow direction PR in FIG. 9.

The actuation of the two solenoid valves 300 and 310 is performed by way of a control device 50 which actuates the two solenoid valves 300 and 310 in opposite directions. Specifically, the actuation of the two solenoid valves 300 and 310 is performed such that, at any point in time, in each case one of the two solenoid valves 300 or 310 is moved into the pressurization position and the respective other solenoid valve 300 or 310 is moved into the rest position. Through alternating switching of the two solenoid valves 300 and 310, the shuttle body 210 can be displaced to the left or to the right. If, for example, by way of the control device 50, the first solenoid valve 300 is switched into the pressurization position and the second solenoid valve 310 is switched into the rest position, the pressure of the positive-pressure source 20 will displace the shuttle body 210 to the right. As a result of the displacement of the shuttle body 210, it is likewise the case that an air column is displaced, which may exit the second solenoid valve 310 via the ventilation port R.

For the return movement of the shuttle body 210 (cf. FIG. 9), the second solenoid valve 310 is moved into the pressurization position and the first solenoid valve 300 is moved into the rest position. In these valve positions, the shuttle body 210 will, owing to the positive pressure of the positive-pressure source 20, move from right to left and force an air column out of the shuttle body actuator 200 and into the surroundings through the ventilation port R of the first solenoid valve 300.

The movement leads to a vibration and thus to a mechanical movement that can be coupled into human or animal tissue.

FIG. 10 shows an exemplary embodiment of an excitation unit 10 which corresponds to the design variant as per FIG. 9 with the exception that, as a pressure source, use is made of a negative-pressure source 20a. The negative pressure of the negative-pressure source 20a is applied by way of the first solenoid valve 300 and the second solenoid valve 310 alternately to the first pressure inlet 201 or to the second pressure inlet 202, whereby the shuttle body 210 moves back and forth in the manner discussed in conjunction with FIG. 9.

FIG. 11 shows an excitation unit 10 which has a positive-pressure source 20, a negative-pressure source 20a, a solenoid valve 400 in the form of a 4/2 directional valve, and a shuttle body actuator 200. The shuttle body actuator 200 may correspond, in terms of its construction, to the shuttle body actuator 200 as per FIGS. 9 and 10, such that, with regard to the design of the shuttle body actuator 200, reference is made to the above explanations relating to FIGS. 9 and 10.

The solenoid valve 400 has two inlet ports P and T, one of which is connected to the positive-pressure source 20 and the other of which is connected to the negative-pressure source 20a.

The solenoid valve 400 furthermore has two outlet ports A and B, of which one is connected to the first pressure inlet 201 of the shuttle body actuator 200 and the other is connected to the second pressure inlet 202 of the shuttle body actuator 200.

The solenoid valve 400 permits two valve positions: in a first valve position, the solenoid valve 400 connects the first pressure inlet 201 of the shuttle body actuator 200 to the positive-pressure source 20 and connects the second pressure inlet 202 of the shuttle body actuator 200 to the negative-pressure source 20a. In this valve position, the shuttle body 210 is moved from left to right in the illustration as per FIG. 1.

In the second valve position, the solenoid valve 400 connects the first pressure inlet 201 of the shuttle body actuator 200 to the negative-pressure source 20a and connects the second pressure inlet 202 to the positive-pressure source 20. In this second valve position, the throttle body 210 is moved from right to left in the illustration as per FIG. 11.

By way of an adjustment of the solenoid valve 400 from the first valve position into the second valve position and vice versa, it is thus possible for the shuttle body 210 to be moved from right to left and from left to right respectively. The movement leads to a vibration and thus to a mechanical movement that can be coupled into human or animal tissue.

The excitation unit 10 as per FIG. 11 has, for the actuation of the solenoid valve 400 or for the adjustment of the valve position of the solenoid valve 400, a control device 50 which can set the respectively desired valve position of the solenoid valve by way of an electrical control signal ST. Otherwise, the above statements made with regard to FIGS. 1 to 10 apply correspondingly.

In summary, the concept of the excitation unit 10 described by way of example in conjunction with FIGS. 1 to 11 consists in the separation of force generation and control mechanism. By contrast to hitherto known actuators, a powerful force source in the form of compressed air, for example, is controlled by way of a preferably fast-switching solenoid valve, for example by way of a function generator. In this case, in the throughflow, short transient air shocks are transmitted onward to a suitable vibration generator which is in contact with the body surface at or in the vicinity of the organ to be examined. The new excitation unit is compatible with all previous technical developments for vibration generation in the field of elastography.

The extremely simple but efficient principle of the excitation unit 10 may—depending on embodiment—have five crucial advantages over the previous actuators from the prior art:

1) Separation into an inexpensive control system and a powerful force source
2) Adequate force reserves through the use of compressed air (for example for the compensation of weak motion encoding gradients or relatively large required penetration depths) or negative pressure
3) Small structural form and universal excitation systems with relatively long range of the shear wave propagation (for example excitation of the brain via neck/thorax) are possible
4) Easy handling and robust construction with industrially proven components
5) The actuation of the solenoid valve can be performed in the low-voltage range (24 V) and thus differs in terms of safety from other systems, which require voltages in the range of >100 V. This will have a positive effect in the approval of the appliance as a medical device.

REFERENCE DESIGNATIONS

10 Excitation unit
20 Positive-pressure source
20a Negative-pressure source
21 Compressed-air reservoir
22 Reducing valve
23 Manometer
24 Vacuum pump
25 Negative-pressure tank
26 Two-position controller
30 Solenoid valve
40 Bellows-cylinder-type actuator
41 Plate
42 Plate
43 Bellows
44 Spring
48 Pressure inlet
50 Control device
60 Cushion-type actuator
61 Cushion wall
63 Cushion interior
64 Non-metallic spring element
70 Drum-type actuator
71 Diaphragm 100 Compressed-air line
200 Shuttle body actuator
201 Pressure inlet
202 Pressure inlet
210 Shuttle body
300 Solenoid valve
310 Solenoid valve
400 Solenoid valve
A Outlet port
B Outlet port
DL Compressed air
F Restoring spring
M Solenoid drive
P Inlet port
PR Arrow direction
R Ventilation port
ST Control signal
T Inlet port
VS Vacuum

The invention claimed is:

1. An elastography device having
at least one excitation unit (10) for generating mechanical tissue movements in human or animal tissue, and
an image-recording device,
wherein the excitation unit (10) has:
at least one gas pressure source (20, 20a),
at least one pressure-dependently operating actuator (40, 60, 70, 200) for generating the mechanical tissue movements,
at least one controllable valve (30, 300, 310, 400) which is arranged between pressure source (20, 20a) and actuator (40, 60, 70, 200) in terms of gas flow and the valve position of which influences the pressure acting on the actuator (40, 60, 70, 200), and
a control device (50) which is connected to a control port of the valve (30, 300, 310, 400) and which actuates the valve (30, 300, 310, 400) and defines the valve position thereof and, in order to generate the mechanical tissue movements, varies the valve position, and thus the pressure acting on the actuator (40, 60, 70, 200), over the course of time, and
wherein the valve (30, 300, 310, 400) is an electrically controllable solenoid valve,
wherein an inlet port of the solenoid valve is connected to the gas pressure source, and
wherein an outlet port of the solenoid valve is connected to the actuator.

2. The elastography device as claimed in claim 1, wherein the valve (30, 300, 310) can be moved into a rest position in which it separates the actuator (40, 60, 70, 200) from the pressure source (20, 20a) and charges the actuator with ambient pressure, in particular connects the actuator to the ambient air in terms of gas flow.

3. The elastography device as claimed in claim 1, wherein the control device (50) is designed so as to move the valve (30, 300, 310) alternately over the course of time into a pressurization position, in which the valve 5 (30, 300, 310, 400) transmits the pressure of the pressure source (20, 20a) onward to the actuator (40, 60, 70, 200), or into a rest position, in which the valve (30, 300, 310) separates the actuator (40, 60, 70, 200) from the pressure source (20, 20a) and charges 10 the actuator with ambient pressure.

4. The elastography device as claimed in claim 1, wherein the control device (50) is designed such that, by actuation of the valve (30, 300, 310, 400), said control device generates at the pressure inlet of the actuator (40, 60, 70, 200) a pressure profile which is of rectangular or pulsed form over the course of time.

5. The elastography device as claimed in claim 1, wherein the pressure source (20, 20a) is a constant-pressure source.

6. The elastography device as claimed in claim 1, wherein the pressure source is a positive-pressure source (20), in particular a compressed-air source.

7. The elastography device as claimed in claim 1, wherein the pressure source is a negative-pressure source (20a), in particular a vacuum device.

8. The elastography device as claimed in claim 1, wherein
a first pressure line connects the pressure source (20, 20a) to the valve (30, 300, 310, 400) and charges the valve (30, 300, 310, 400) with a constant pressure, and
a second pressure line connects the valve (30, 300, 310, 400) to the actuator (40, 60, 70, 200) and charges the actuator (40, 60, 70, 200), in a manner dependent on the valve position of the valve (30, 300, 310, 400), with a pressure which is variable over the course of time.

9. The elastography device as claimed in claim 1, wherein
wherein the at least one controllable valve comprises two valves,
the actuator (200) has two pressure inlets which are each connected by way of one of the two valves (300, 310) to the pressure source (20, 20a), and
the control device (50) is designed such that, to generate the mechanical tissue movements, it moves the two valves (300, 310) in each case alternately over the course of time into a pressurization position, in which the valve (300, 310) transmits the pressure of the pressure source (20, 20a) onward to the actuator (200), or into a rest position, in which the valve (300, 310) separates the actuator (200) from the pressure source (20, 20a) and charges the actuator with ambient pressure, the two valves (300, 310) being actuated in each case oppositely over the course of time such that in each case one of the two valves (300, 310) is situated in the pressurization position and the respective other is situated in the rest position.

10. The elastography device as claimed in claim 1, wherein
the actuator (200) has a first pressure inlet and a second pressure inlet,
the valve (400), in a first valve position, connects the first pressure inlet to a positive-pressure source (20) and connects the second pressure inlet to a negative-pressure source (20a) and, in a second valve position, connects the first pressure inlet to the negative-pressure source (20a) and connects the second pressure inlet to the positive-pressure source (20), and
the control device (50) is designed such that, to generate the mechanical tissue movements, it switches the valve (400) alternately from the first valve position into the second valve position and from the second valve position into the first valve position.

11. The elastography device as claimed in claim 1, wherein the actuator is a bellows-cylinder-type actuator (40), a cushion-type actuator (60), a drum-type actuator (70) or shuttle body actuator (200), in particular a shuttle piston actuator.

12. The elastography device as claimed in claim 1, wherein the valve comprises a 3/2 directional valve.

13. An elastography method, in which
mechanical tissue movement is generated in human or animal tissue by way of at least one excitation unit (10), and images of the tissue are recorded by way of an image-recording device, wherein,
by way of a pressure source (20, 20*a*), pressure is generated and transmitted onward to at least one controllable valve (30, 300, 310, 400) which is connected, at the outlet side, to a pressure-dependently operating actuator (40, 60, 70, 200), and the valve position of the valve (30, 300, 310, 400) is varied over the course of time, whereby the actuator (40, 60, 70, 200) generates the mechanical tissue movement, wherein the valve (30, 300, 310, 400) is an electrically controllable solenoid valve, wherein an inlet port of the solenoid valve is connected to the gas pressure source, and wherein an outlet port of the solenoid valve is connected to the actuator.

\* \* \* \* \*